(12) United States Patent
Mouw

(10) Patent No.: US 6,746,469 B2
(45) Date of Patent: Jun. 8, 2004

(54) BALLOON ACTUATED APPARATUS HAVING MULTIPLE EMBOLIC FILTERS, AND METHOD OF USE

(75) Inventor: Steven L. Mouw, Campbell, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 458 days.

(21) Appl. No.: 09/845,788

(22) Filed: Apr. 30, 2001

(65) Prior Publication Data

US 2002/0161390 A1 Oct. 31, 2002

(51) Int. Cl.[7] .............................................. A61M 29/00
(52) U.S. Cl. ...................... 606/200; 606/198; 606/192
(58) Field of Search ............................... 606/200, 159, 606/198, 191, 194; 623/2.12, 2.17, 2.18, 2.19

(56) References Cited

U.S. PATENT DOCUMENTS

| | | | |
|---|---|---|---|
| 5,108,419 A | * | 4/1992 | Reger et al. ................ 606/200 |
| 5,827,324 A | | 10/1998 | Cassell et al. |
| 5,911,734 A | | 6/1999 | Tsugita et al. |

\* cited by examiner

Primary Examiner—Henry Bennett
Assistant Examiner—Camtu Nguyen
(74) Attorney, Agent, or Firm—Fulwider Patton Lee & Utecht, LLP

(57) ABSTRACT

An apparatus having multiple filters for capturing embolic material released from a lesion in an occluded body vessel being treated with an interventional procedure. The filters are placed downstream from the lesion, and the porosity of the filters decreases for each succeeding filter downstream from the lesion. Before encountering the filters, the embolic material passes a unidirectional barrier acting as a one-way valve to prevent backflow. The unidirectional barrier and filters are positioned along a plurality of arms. The arms may be fabricated from a memory metal, and the memory position of the plurality of arms is a collapsed position surrounding a common longitudinal axis. The apparatus includes an expansion member, such as a balloon, which inflates to move the plurality of arms radially outward to deploy the filters. Embolic material passes through the unidirectional barrier and is trapped between the layers of filters. When the balloon is deflated, the plurality of arms return to the memory position, collapse the unidirectional barrier and the filters, and embolic material remains trapped between the layers of filters.

19 Claims, 3 Drawing Sheets

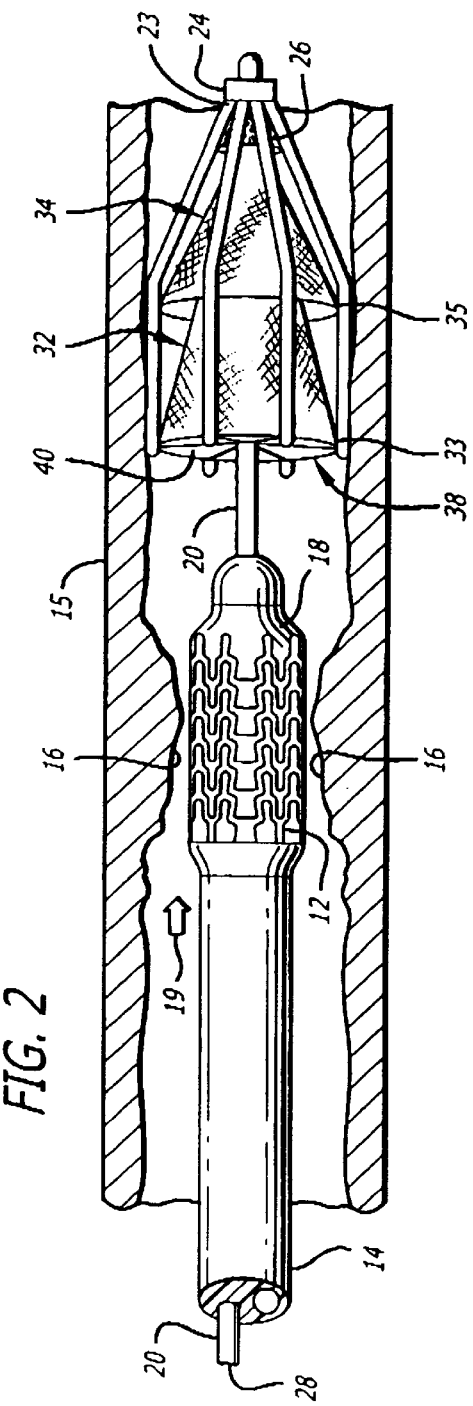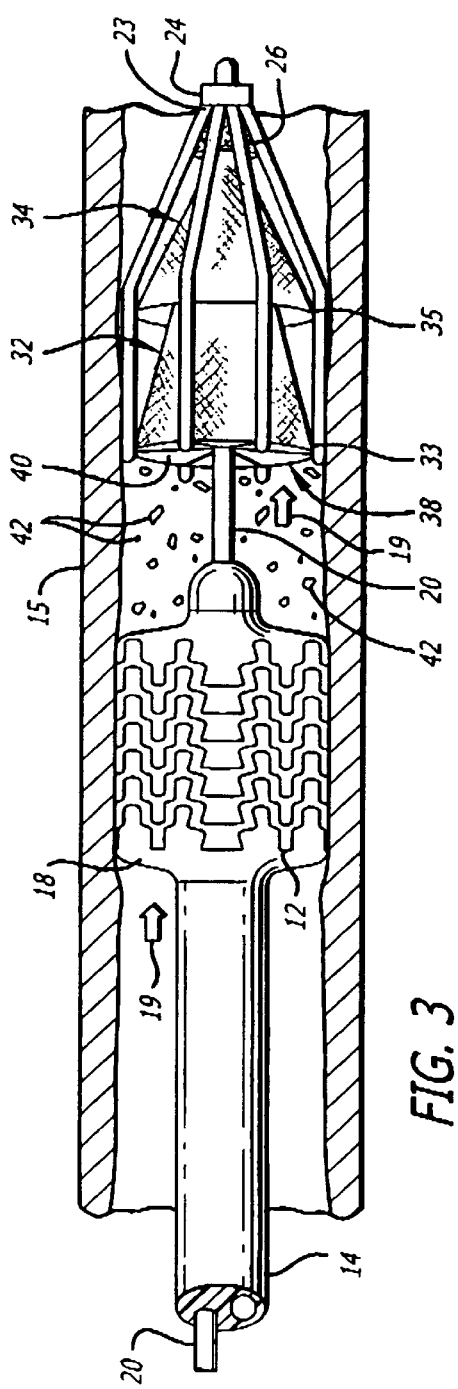

BALLOON ACTUATED APPARATUS HAVING MULTIPLE EMBOLIC FILTERS, AND METHOD OF USE

BACKGROUND OF THE INVENTION

The present invention relates generally to an apparatus which can be used when an interventional procedure is being performed in a stenosed or occluded region of a blood vessel to capture embolic material that may be created and released into the bloodstream during the procedure. The apparatus of the present invention is particularly useful when performing balloon angioplasty, stenting procedures, laser angioplasty or atherectomy in critical vessels, such as the carotid arteries, where the release of embolic debris into the bloodstream can occlude the flow of oxygenated blood to the brain or other vital organs. It is to be understood that the apparatus and method of this invention can be used in numerous other vascular interventional procedures.

Numerous procedures have been developed for treating occluded blood vessels to allow blood to flow without obstruction. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel.

Another procedure is laser angioplasty which utilizes a laser to ablate the stenosis by super heating and vaporizing the deposited plaque. Atherectomy is yet another method of treating a stenosed blood vessel in which a cutting blade or other specialized burr is rotated to shave the deposited plaque from the arterial wall.

In another widely practiced procedure, the stenosis can be treated by placing a device known as a stent into the stenosed region to hold open and sometimes expand the segment or blood vessel or other arterial lumen. Stents are particularly useful in the treatment of repair of blood vessels after a stenosis has been compressed by percutaneous transluminal coronary angioplasty (PTCA), percutaneous transluminal angioplasty (PTA) or removal by atherectomy or other means. Stents are delivered in a compressed condition to the target site, and then are deployed at the target location into an expanded condition to support the vessel and help maintain it in an open position.

In the process of treating such blood vessels at the location of the lesions, embolization of plaque (embolic debris) may occur during the treatment. Detached from the lesion, the embolic debris enters the bloodstream and subsequently migrate through the patient's vasculature. Larger embolic debris can obstruct a vessel and cause ischemia, apoptosis, or vessel necrosis.

To allow the use of more aggressive treatment of vascular lesions, procedures have also been developed for preventing embolic debris from flowing through the vessels with the blood. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists. Another approach involves the use of a vacuum catheter which provides temporary suction to capture and remove embolic debris from the bloodstream. However, the vacuum catheter may not remove all of the embolic material from the bloodstream, and the suction produced by the vacuum catheter could cause trauma to the patient's vasculature.

Another technique involves the placement of a filter downstream from the treatment site to capture embolic debris before it reaches the smaller blood vessels downstream. The placement of a filter in the patient's vasculature during treatment of the vascular lesion can reduce the movement of the embolic debris in the bloodstream. Such filters are usually delivered in a collapsed position through the patient's vasculature and then are expanded once in place in the patient's body vessel to trap the embolic debris. The filter can then be collapsed to remove the filter (with the trapped embolic debris) from the body vessel. However, there have been difficulties associated with filtering systems, such as during the expansion and collapsing of the filter within the body vessel. It is possible for some of the trapped embolic debris to escape from the filter as the filter is being collapsed and removed from the body vessel.

There is a need in the art for an apparatus and method which can be utilized to treat an occluded vessel and capture embolic material that may be formed during the vascular procedure. Such an apparatus and method should also prevent the embolic material from escaping from the filter during the time that the filter is being collapsed or removed from the blood vessel (e.g., the carotid arteries). Such an apparatus and method should be relatively easy and safe to deploy, and be easily removed from the vasculature with minimal adverse impact or immunological response to the patient.

SUMMARY OF THE INVENTION

The present invention is directed to embolic filtering apparatus. The embolic filtering apparatus comprises a plurality of arms having a proximal end, a distal end, and a first segment end between the proximal end and the distal end, and an expandable member located at the distal end of the plurality of arms, wherein inflating the expandable member causes the plurality of arms to move radially outward. An unidirectional barrier is attached to the plurality of arms to capture embolic material when the plurality of arms are moved radially outward by the expandable member. The unidirectional barrier allows embolic material to pass in the direction towards the filter, but not in the opposite direction.

In one aspect of the embolic filtering apparatus, a first filter is located at the proximal end of the plurality of arms; a second filter located at the first segment end of the plurality of arms; wherein the first filter has a larger porosity than the second filter such that the second filter is capable of screening smaller embolic material than the first filter, allowing embolic material to be captured between the first filter and the second filter.

In another aspect of the embolic filtering system, the unidirectional barrier is located at the proximal end of the plurality of arms such that the unidirectional barrier allows embolic material to pass in the direction toward the filter, but not in the opposite direction.

In yet another aspect of the embolic filtering system, the plurality of arms are composed of a memory metal having a memory position, and the memory position represents the plurality of arms collapsed toward one another along a longitudinal axis. In its memory position, the plurality of arms are relatively straight. The plurality of arms collapse toward one another when the expandable member is deflated. The plurality of arms can also have a thickness that is greater at the distal end than at the proximal end.

In another aspect of the embolic filtering system, the filters limit the radial movement of the plurality of arms when the expandable member is expanded. The filters can be coated with an anti-coagulant to minimize the potentiality of clot formation.

The method of using the embolic filter apparatus comprises the steps of inserting an embolic filter device into a vessel; advancing the embolic filter device to a position downstream of the lesion to be treated in the vessel; expanding a expandable member to move a plurality of arms radially outward and deploy an unidirectional barrier and a first filter; and capturing in the embolic filter device embolic material that may be produced during treatment of the lesion. In use, the unidirectional barrier allows embolic material to pass in the direction toward the first filter, and not in the opposite direction.

In another aspect of the method of using the embolic filter apparatus, a second filter, capable of screening smaller embolic material than the first filter, is also deployed when the expandable member is expanded to move the plurality of arms radially outward; and embolic material is captured between the deployed first and second filters.

In another aspect of the method of using the embolic filter apparatus, the plurality of arms is composed of a memory metal having a memory position, and the memory position represents the plurality of arms collapsed toward one another along a longitudinal axis.

It is to be understood that the present invention is not limited by the embodiments described herein. The present invention can be included on a guide wire, on the delivery catheter, or on a separate catheter. The present invention can also be used in arteries, veins, and other lumen in the body. Other features and advantages of the present invention will become more apparent from the following detailed description of the invention, when taken in conjunction with the accompanying exemplary drawings.

BRIEF DESCRIPTION OF THE DRAWINGS

FIG. 2 is a side elevational view, similar to that shown in FIG. 1, wherein the embolic filter is expanded.

FIG. 3 is a side elevational view, similar to that shown in FIG. 1, wherein the stent is expanded by the balloon delivery catheter and embolic material are produced.

DETAILED DESCRIPTION OF THE EMBODIMENTS

Figure 1:
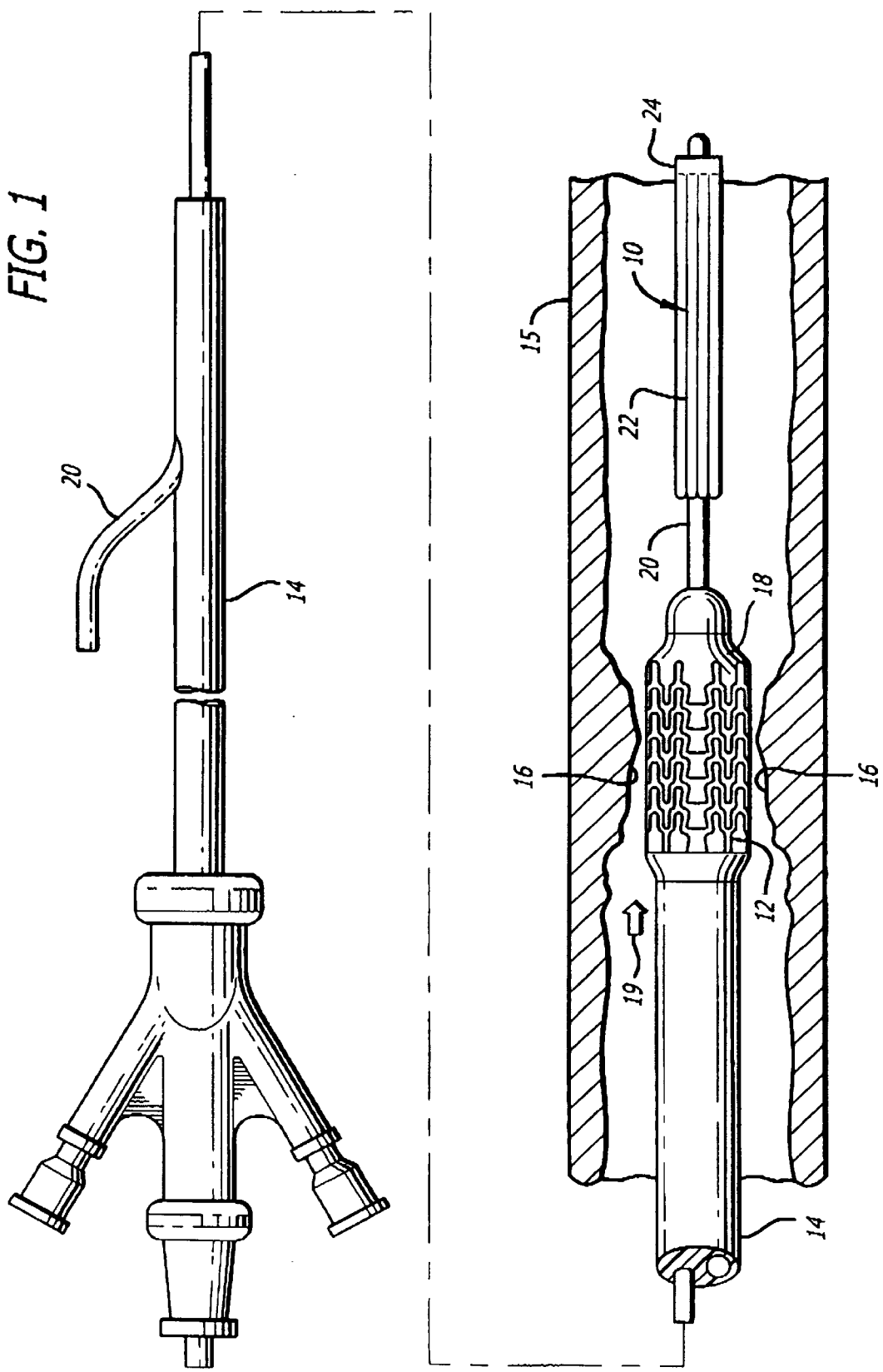
FIG. 1 is a side elevational view, partially in section, depicting a guide wire having an embolic filter device embodying features of the present invention with a stent and balloon delivery catheter in a body vessel.

The present invention is directed to an apparatus and method for efficiently and effectively capturing embolic debris which may be released into the bloodstream when performing an interventional procedure in a blood vessel or other body lumen. The embodiments of the system and method are illustrated and described herein by way of example only and not by way of limitation. While the present invention is described in detail as applied to the carotid arteries of the patient, and the disclosed interventional procedure is directed to a stenting procedure, those skilled in the art will appreciate that it can also be used in other body lumina as well, such as the coronary arteries, renal arteries, saphenous veins and other peripheral arteries. Additionally, the present invention can be utilized when performing any one of a number of interventional procedures, including, but not limited to, balloon angioplasty, laser angioplasty or atherectomy.

Referring now to the drawings, wherein like reference numerals denote like or corresponding parts throughout the drawing figures, an embolic filtering apparatus 10 is provided for capturing embolic material which may be released into a blood vessel during a therapeutic interventional procedure. Additional details regarding the particular structure and shape of the embolic filtering system are provided below.

FIG. 1 illustrates an embodiment of an embolic filtering apparatus 10 incorporating features of the present invention. FIG. 1 also illustrates a stent 12 which is mounted onto a balloon delivery catheter 14 for treating an occluded artery 15, such as the carotid artery or other body vessel. The artery 15, as shown in FIG. 1, has a lesion 16 which has occluded a portion of the arterial passageway. The delivery catheter 14 has an expandable portion (a balloon) 18 for expanding the stent 12. The delivery catheter 14 is tracked over a guide wire 20 through a guide wire lumen in the delivery catheter 14. A hypotube having appropriate dimensions can be used to fabricate the guide wire 20. The balloon portion 18 carrying the stent 12 is positioned at the lesion 16 to be treated in the artery 15. The therapeutic interventional procedure may comprise the implantation of the stent 12 to increase the diameter of the occluded artery, to hold open the artery, and to increase the flow of blood therethrough. The direction of the antegrade flow of blood downstream is indicated by arrow 19.

In the particular embodiment illustrated in FIG. 1, the embolic filtering apparatus 10 is part of the guide wire 20 over which the delivery catheter 14 is tracked. It is to be understood that the embolic filtering apparatus is not limited to placement on a guide wire, and may be part of the delivery catheter itself, or on a separate catheter introduced and placed downstream of the area of treatment. Thus, the embolic filter apparatus 10 can be based on a guide wire platform, catheter platform, or any other suitable platform that would allow proper deployment and use of the filter system downstream of an interventional procedure. The embolic filtering apparatus 10 includes a plurality of arms 22 which are normally in a collapsed position around the shaft of the guide wire 20. The distal end 23 of each arm 22 can be secured to the guide wire 20 by an annular ring 24 disposed about the distal end of the plurality of arms 22 near the distal tip of the guide wire 20. The distal ends 23 of the plurality of arms can also be secured to the guide wire by an adhesive, welding, brazing, or other suitable form of connection. Where the guide wire includes a coil tip, the coil tip can be extended to encircle the distal ends 23 of the plurality of arms 22, which would avoid the need for a separate ring to couple the plurality of arms to the guide wire. The coil tip can be secured to the guide wire by an adhesive, welding, brazing, or other suitable form of connection. It is to be understood that the distal end of the plurality of arms can be secured to the guide wire in any suitable manner to provide a pivot-like connection.

Arms 22 can be composed of a resilient material having shape memory. One suitable material is a memory metal such as a nickel-titanium alloy. The memory position of the plurality of arms is relatively straight, and forms a collapsed position around a longitudinal axis, such as that defined by the shaft of the guide wire 20. This provides for a low profile as the embolic filtering apparatus 10 is being delivered by the guide wire 20 to the apparatus downstream location from the lesion 16.

As illustrated in FIG. 2, the embolic filtering apparatus 10 is deployed by expanding an actuator member (for example, a balloon) 26 located at the distal end of the plurality of arms 22 near the distal tip of the guide wire 20. The actuator balloon 26 is inflated through an inflation lumen 28 extending through the guide wire 20. The inflation lumen 28 carries a suitable fluid for inflating the actuator balloon 26. The actuator balloon 26 can be fabricated from a suitable material, such as material used for balloons on coronary balloon angioplasty catheters. For example, polymers such as ePTFE, polyurethane, nylon, or polyethylene are suitable materials.

The expansion of inflating the actuator balloon 26 causes the plurality of arms 22 to move radially outward from the longitudinal axis defined by the shaft of the guide wire 20, with the distal ends 23 of the plurality of arms 22 forming a pivot near the distal tip of the guide wire 20. Although the actuator balloon 26 is illustrated as having a conical-like shape, the actuator balloon 26 can be fabricated to have a oval shape, spherical shape, or any suitable shape for causing the radial movement of the plurality of arms 22. Arms 22 have an appropriate thickness to allow radial movement to engage the walls of vessel 15. For example, arms 22 may have a thickness ranging from one micron to several millimeters, depending on the size of the vessel being treated. The thickness of arms 22 need not be uniform, and can be varied along its length. For example, the arm may be thicker at the distal end than at its proximal end. Less deformation may occur at the thicker distal end of the arms when the actuator balloon is inflated to expand the arms.

Having been actuated by the inflation of the actuator balloon 26, arms 22 display segmentation in their radial deployment. The segment at the proximal end of the plurality of arms 22, which is furthest away from the actuator balloon 26 at the distal ends 23 of the plurality of arms 22, exhibits the greatest radial movement and engages the wall of artery 15 being treated. The segments of the arms 22 closer to the actuator balloon 26 may exhibit less radial movement. Preferably, the segments of the arms 22 engage the wall of the artery. The thickness of arms 22 may change or vary along the segment points along the length of arms 22. For example, the thickness of arms 22 increases near the distal end where the actuator balloon 26 is located. The thinner dimensions of arms 22 towards the proximal end allows for more bending of the arms 22.

Filters 32 and 34 are attached to the plurality of arms 22 at different segment points along the length of arms 22. The segment points should be closely spaced together. The first filter 32 is secured to a first segment 33 on or near the proximal end of the arms 22, and the second filter 34 is secured to a second segment 35 of the arms 22 between first segment and the distal end of the arms 22. The segments are preferably located on the thicker portion of the arms near the distal end of the arms. The filters 32 and 34 may be attached to a common point on the guide wire such near the distal end or adjacent to the actuator balloon 26. In this manner the filters 32 and 34 will nest or overlap with one another at least partially along the length of the guide wire.

The filters 32 and 34 are secured to the plurality of arms 22 and the shaft of the guide wire 20 by polyurethane adhesives, silicon adhesives, welding materials, or any other suitable bonding techniques. The first filter 32 is secured to a first segment 33 on or near the proximal end of the arms 22, and the second filter 34 is secured to a second segment 35 of the arms 22 between first segment and the distal end of the arms 22. The first segment 33 and the second segment 35 should be close spaced to one another. The filters 32 and 34 form a generally conical shape when deployed by the radial movement of the plurality of arms 22. Being affixed to arms 22 and the guide wire 20, the filters 32 and 34 limit the expanded diameter defined by the radial movement of arms 22 when the actuator balloon 26 is inflated. In accordance with the invention, the filters 32 and 34 can be dimensioned to limit expansion of the arms at those segment point to predetermined diameters. Preferably, the first and second segments 33 and 35 of the arms 22 will engage the wall of the artery 15.

It is to be understood that the filters can be affixed to any suitable location along the length of the guide wire. For example, the filters may be affixed to locations along the length of the guide wire which would minimize or avoid overlap between adjacent filters so that a low delivery profile is achieved when the embolic filtering system is collapsed.

Figure 4:
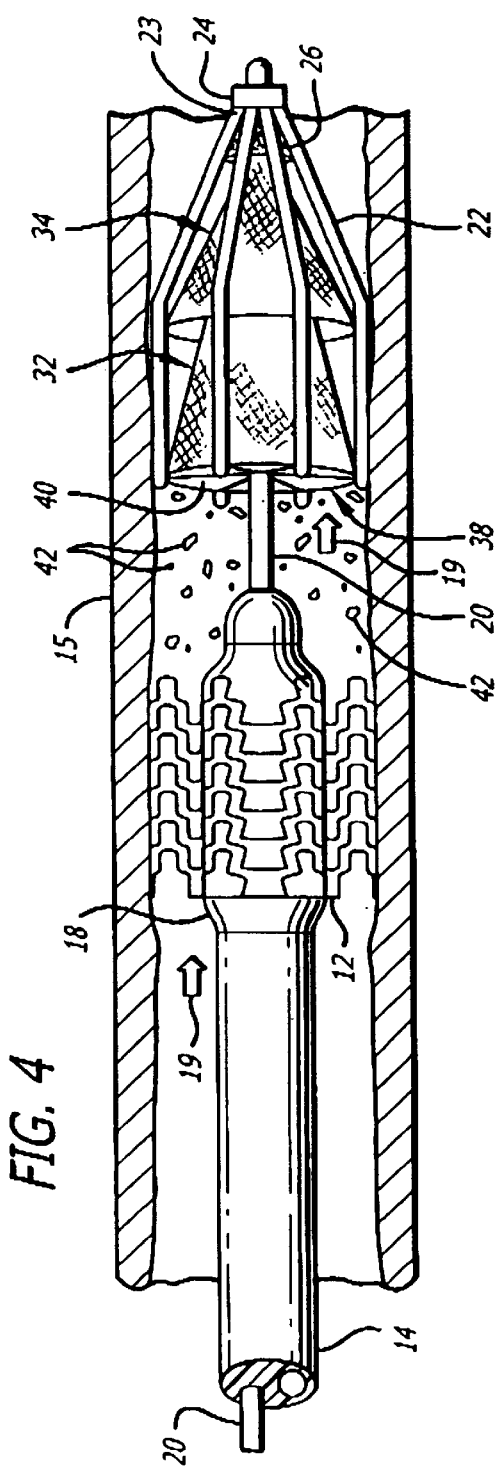
FIG. 4 is a side elevational view, similar to that shown in FIG. 1, wherein the balloon delivery catheter has been deflated, and embolic material are captured by the embolic filter device.

Although two filters 32 and 34 are illustrated in FIGS. 2 through 4, any number of filter layers of varying porosity can be employed. For example, there can be from one to thirty-six, or more, filter layers employed in the embolic filter system.

The filters 32 and 34 can have any suitable length or diameter for the vessel being treated. The filters 32 and 34 can be manufactured from ePTFE, polyurethane, polycarbonate, polyethylene, nylon, or any suitable material which can be fabricated to have a certain porosity. By way of example, the first filter 32 could contain 500 micron pores while the second filter 34 could contain 300 micron pores. For example, a third filter containing 100 micron pores may be used to capture even smaller embolic material. These dimensions are given by way of example and are not limitations. In this manner, each succeeding filter will have a progressively decreasing porosity. Other materials such as buckeye balls (nanotubes), protein chains, and other materials could also be used as filtration materials. Fabrication of the filters 32 and 34 from suitably flexible mesh-like material would assist in avoiding impeding the collapse of the plurality of arms 22 when the actuator balloon 26 is deflated. Drug compounds such as heparin, IIb/IIIa inhibitors, and other blood thinners and anti-coagulants can be bonded to the filters. The use of a drug, such as covalently bonded low molecular weight heparin, with the filter would allow blood to flow freely through the filter while reducing the possibility of clot formation.

In addition to the filters 32 and 34, a unidirectional barrier 38 may be attached to arms 22. The unidirectional barrier 38 is located at the proximal end of the plurality of arms 22. In the embodiment shown in FIGS. 1–4, the first filter 32 is nested between the second filter 34 and the unidirectional barrier 38. When deployed by the radial movement of the plurality of arms, the unidirectional barrier 38 forms a generally conical shape which directs blood flow towards the filters. As indicated by arrow 19, the flow of blood encounters the unidirectional barrier 38 before the filters 32 and 34. The antegrade flow of blood opens the unidirectional barrier 38, and the retrograde flow of blood closes the unidirectional barrier 38. In this manner, the unidirectional barrier 38 acts as a one-way valve to prevent retrograde or backflow so that the trapped embolic debris does not escape through the open end of the filters 32 and 34. Embolic material should remain trapped between the filters and should not enter the bloodstream as the embolic filtering apparatus 10 is being collapsed for removal from the patient. Although the unidirectional barrier 38 is shown having a generally conical shape, it can take on any suitable configuration that would prevent backflow. For example, the unidirectional barrier 38 can act in a manner similar to the valve in the veins or in the heart, and take the form of a bicuspid valve, or a tricuspid valve. The positive pressure from the antegrade flow of blood would open the leaflets 40 of the bicuspid or tricuspid valve of the unidirectional barrier 38 in order to allow embolic material to pass toward the filters. Retrograde flow creates negative pressure against the conical gradient of the valve, collapsing the leaflets 40 against one another to close the valve sufficiently to prevent embolic debris from escaping. Alternatively, the unidirectional barrier may employ a plurality of one-way valves or valvular pores formed in the flexible barrier. In this manner, the unidirectional barrier would be similar to the filters except that the valvular pores would not be mere openings, but valve-like in structure. The valvular pores can be bicuspid, tricuspid, or have any suitable configuration that would allow antegrade flow and prevent retrograde flow. While the general size of valvular pores should be larger than the largest porosity of the filters, the sizes of valvular pores need not be uniform and can be varied along the surface of the unidirectional barrier. The unidirectional barrier should be fabricated from a flexible material so as to allow the arms to collapse when the actuator balloon 26 is deflated. Suitable material for the unidirectional barrier include ePTFE, polyurethane, and polyethylene. Drug compounds such as heparin, IIb/IIIa inhibitors, and other blood thinners and anti-coagulants can also be bonded to the unidirectional barrier 38.

As illustrated in FIG. 3, when the balloon 18 is inflated to compress the lesion and implant the stent 12 into the vessel wall, embolic material and debris 42 may be produced which then flow downstream towards the expanded unidirectional barrier 38 and the filters 32 and 34 of the embolic filtering apparatus 10. Embolic debris 42 first passes the unidirectional barrier 38. There is a space between the unidirectional barrier 38 and the next succeeding filter 32. A significant portion of embolic debris will remain captured in this space. There is also space between the first filter 32 and the next succeeding filter 34. Again, the second filter 34 has a smaller porosity than that of the filter 32. Progressively smaller and smaller embolic debris pass through and are captured in the spaces between successive layers of filters as blood flows through the embolic filtering apparatus.

Figure 5:
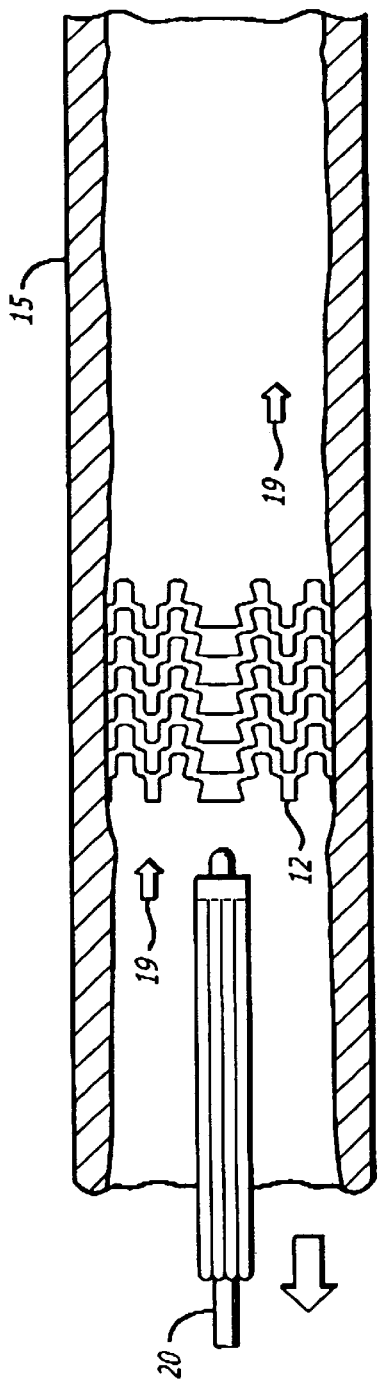
FIG. 5 is a side elevational view, similar to that shown in FIG. 1, wherein the embolic filter device is in a collapsed position and is being retracted from a vessel with the filter retaining any embolic material which may have been generated during the procedure.

As illustrated in FIG. 4, when the balloon 18 is deflated, antegrade flow is increased and the remaining embolic debris is carried through the unidirectional barrier 38 to be trapped or captured between the successive layers of the filters. The unidirectional barrier 38 help prevent embolic debris from escaping through backflow. As previously discussed, the negative pressure from retrograde or backflow closes or collapses the leaflets 40 of the unidirectional barrier 38, creating a barrier that closes the opening to the first filter 32. After capturing the embolic debris between the unidirectional barrier 38 and the filters 32 and 34, the actuator balloon 26 is deflated to allow the plurality of arms 22 to straighten and collapse back to its closed memory position around the longitudinal axis of the guide wire 20. The embolic debris remains captured between the collapsed unidirectional barrier 38 and the filters 32 and 34. After the procedure is completed, as illustrated in FIG. 5, the embolic apparatus system 10 is withdrawn from the vasculature while the stent 12 remains at treatment site to help prevent restenosis and maintain the enlarged vessel opening.

While illustrated and described herein in terms of its use in the intravascular treatment of arteries, it will be apparent to those skilled in the art that the embolic filtering system can be used on other delivery platforms, and can be used in other lumina in the body. Other mechanisms can also be used to deploy the filters and the unidirectional barrier from a collapsed position to an expanded position. One such mechanism is an open-mouthed tubular stocking having a drawstring to close the mouth of the stocking, and resilient ribs are attached to the filter elements to spread and open the filters when the mouth of the stocking is opened. Another mechanism would have the filter elements deploy by removing a restraining sheath or any other method known in the art. Other modifications and improvements may be made without departing from the scope of the invention.

What is claimed is:

1. An apparatus for filtering embolic material, comprising:
a plurality of arms, each arm having a proximal end and a distal end;
a expandable member located near the distal end of each of the arms, wherein the expandable member causes the plurality of arms to move radially outward;
a first filter located at a first segment point near the proximal end and the distal end of each of the arms; and
a unidirectional barrier located adjacent to the first filter at the proximal end of each of the arms such that the unidirectional barrier allows embolic material to pass in a flow direction toward the first filter, and not in an opposite flow direction.

2. The apparatus of claim 1, further comprising:
a second filter located at a second segment joint of each of the arms;
wherein the first filter has a porosity higher than the porosity of the second filter such that the second filter is capable of capturing embolic material which may pass through the first filter.

3. The apparatus of claim 2, wherein:
the first filter and the second filter limit the radial movement of the plurality of arms such that the diameter defined by the first segment point of each of the arms is substantially the same as the diameter defined by the second segment point of each of the arms.

4. The apparatus of claim 1, wherein:
an anti-coagulant is bound to the first filter.

5. The apparatus of claim 1, wherein:
the plurality of arms is composed of a memory metal and has a memory position, and the memory position represents the plurality of arms collapsed toward one another along a longitudinal axis.

6. The apparatus of claim 1, wherein:
each arm has a greater thickness at the distal end than at the proximal end.

7. An apparatus for filtering embolic material, comprising:
a first filter having a first porosity;
a unidirectional barrier arranged to allow embolic material to pass in the direction toward the first filter, and not in the opposite direction; and means for deploying the first filter and the unidirectional barrier from a collapsed position to an expanded position.

8. The apparatus of claim 7, wherein:

the means for deploying includes a plurality of arms having a proximal end, a distal end, and a first segment point between the proximal end and the distal end, wherein the unidirectional barrier is located at the proximal end of the plurality of arms, and the first filter is located at the first segment point of the plurality of arms; and an expandable member located near the distal end of the plurality of arms, wherein inflating the expandable member causes the plurality of arms to move radially outward.

9. The apparatus of claim 8, further comprising:

a second filter, the second filter having a smaller porosity than the first filter such that the second filter is capable of screening smaller embolic material than the first filter; and the plurality of arms includes a second segment point between the first segment point and the distal end, wherein the second filter is located at the second segment point of the plurality of arms, and embolic material is captured between the first filter and the second filter.

10. The apparatus of claim 9, wherein:

the first filter and the second filter limit the radial movement of the plurality of arms such that the diameter defined by the first segment point of each of the arms is substantially the same as the diameter defined by the second segment point of each of the arms.

11. The apparatus of claim 8, wherein:

the plurality of arms is composed of a memory metal and has a memory position, and the memory position represents the plurality of arms collapsed toward one another along a longitudinal axis.

12. The apparatus of claim 8, wherein:

the plurality of arms have a greater thickness at the distal end than at the proximal end.

13. The apparatus of claim 7, wherein:

an anti-coagulant is bound to the first filter.

14. A method of filtering embolic material, comprising:

inserting an embolic filter device into a body vessel, wherein the embolic filter device includes a plurality of arms having a proximal end, a distal end, and a first segment point between the proximal end and the distal end, a expandable member located at the distal end of the plurality of arms, a first filter located at the first segment point of the plurality of arms, and a unidirectional barrier located at the proximal end of the plurality of arms;

advancing the embolic filter device to a position downstream of the lesion to be treated in the blood vessel;

expanding the expandable member to move the plurality of arms radially outward and deploy the first filter; and capturing, in the embolic filter device, embolic material produced during treatment of the lesion, wherein embolic material passes the unidirectional barrier in the direction toward the first filter, and not in the opposite direction, and the first filter screens embolic material of a certain size.

15. The method of claim 14, wherein:

the embolic filter device further includes a second filter capable of screening smaller embolic material than the first filter; and the capturing of embolic material further includes capturing embolic material between the first filter and the second filter.

16. The method of claim 14, wherein:

the expanding of the expandable member includes inflating the expandable member with a fluid.

17. The method of claim 16, further comprising:

deflating the expandable member, wherein the plurality of arms collapse toward one another.

18. The method of claim 17, wherein:

the plurality of arms is composed of a memory metal and has a memory position, and the memory position represents the plurality of arms collapsed toward one another along a longitudinal axis when the expandable member is deflated.

19. The method of claim 14, wherein:

the capturing of embolic material further includes inhibiting coagulation with an anti-coagulant bound to the first filter.

* * * * *